United States Patent [19]

Ovchinnikov et al.

[11] 4,395,399
[45] Jul. 26, 1983

[54] GLYCOPEPTIDES AND METHOD FOR PREPARING SAME

[75] Inventors: Jury A. Ovchinnikov; Vadim T. Ivanov; Larisa I. Rostovtseva; Tatyana M. Andronova; Irina B. Sorokina; Veronika P. Malkova, all of Moscow, U.S.S.R.

[73] Assignee: Institut Bioorganicheskoi Khimii Imeni M.M. Shemyakina Akademii Nauk SSSR, Moscow, U.S.S.R.

[21] Appl. No.: 956,538

[22] Filed: Nov. 1, 1978

[30] Foreign Application Priority Data

Nov. 2, 1977 [SU] U.S.S.R. .................. 2543268

[51] Int. Cl.$^3$ .................. A61K 37/02; C07C 103/52; C07G 7/00
[52] U.S. Cl. .................. 424/177; 260/112.5 R; 424/88
[58] Field of Search .................. 260/112.5 R; 424/180, 424/177; 536/1, 4, 18

[56] References Cited

U.S. PATENT DOCUMENTS

| | | | |
|---|---|---|---|
| 4,094,971 | 6/1978 | Chedid et al. | 260/112.5 R |
| 4,101,536 | 7/1978 | Yamamura et al. | 260/112.5 R |
| 4,101,649 | 7/1978 | Adams nee Chosson | 260/112.5 R |
| 4,110,434 | 8/1978 | Jolles et al. | 260/112.5 R |

OTHER PUBLICATIONS

Elloys, F., et al., Biochem. Biophys. Res. Comm., vol. 59, 1974, pp. 1317-1325.
Kusumoto, S., et al., Tetrahedron Letters, No. 45, pp. 4407-4410, 1978.
Bogdanov et al., FEBS Letters, vol. 57, No. 3, 259-261, 1975.
Sharon et al., J. Biol. Chem., vol. 241, 223-241, 1966.
Merser et al., Tetrahedron Letters, No. 13, pp. 1029-1032, 1973.
Lefrancier et al., Prog. Chem. Org. Nat. Prod., vol. 40, pp. 1, 4-9, 1981.
Durette, P., et al., Carbohydrate Research, vol. 77, pp. $C_1$-$C_4$, 1979.
Kiso, M., et al., Carbohydrate Research, vol. 83, pp. $C_8$-$C_{11}$, 1980.

*Primary Examiner*—Blondel Hazel
*Attorney, Agent, or Firm*—Ladas & Parry

[57] ABSTRACT

Glycopeptides according to the present invention have the formula:

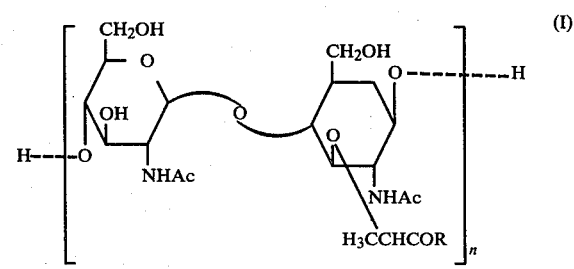

wherein $n=1$ or 2; R is a residue of an aminoacid or linear peptides built of 2 to 5 amino acid residues.

These compounds are prepared by the method involving condensation of unblocked muramyl-containing N-acetylamino-sugars of the formula:

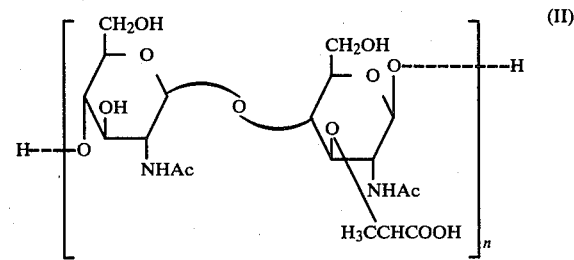

wherein $n=1$ or 2, with blocked aminoacids or peptides.

The method of this invention makes it possible to produce synthetic glycopeptides manifesting a biological activity. These compounds possess an antitumor and adjuvant activity.

9 Claims, No Drawings

GLYCOPEPTIDES AND METHOD FOR PREPARING SAME

The present invention relates to the art of biologically active compounds and, more specifically, to glycopeptides and a method for preparing same.

FIELD OF THE INVENTION

Glycopeptides constitute a broad class of organic compounds comprising substances including the sugar part and the peptide part. Cell walls of bacteria are constituted by glycopeptides. The sugar part of glycopeptides incorporates an unusual carboxyl-containing aminosugar-2-acetamido-3-O-/D-1'-carboxyethyl/-2-deoxy-β-D-glucopyranose generally referred to as N-acetylmuramic acid (MurNAc) and found only in cell walls of bacteria.

Glycopeptides of bacterial cell walls comprise gigantic polymeric molecules composed of alternating units of a disaccharide GlcNAc/1→4/MurNAc[N-acetyl-glucosaminyl/1→4/N-acetylmuramic acid] with peptides of a similar structure bonded with muramic acid (so-called basic peptide chains). Rigidity of the cell wall structure of bacteria is due to peptide bonds (or peptide bridges) between basic peptide chains. By means of a specific enzymatic hydrolysis it is possible to break-up certain bonds in a polymeric molecule of glycopeptides of cell walls of bacteria and obtain glycopeptide fragments of a various length and various structure /1. Ghuysen J.-M., Bact. Rev. 32, No. 4, 425 (1968), 2. Schliefer K. H., Kandler O., Bact. Rev. 36, No. 4, 407, (1972)/.

Until recently it has been believed that the role of glycopeptides of cell walls of bacteria resides merely in providing rigidity of the cell walls for protection of the bacterial cell from the effect of the ambient medium. However, with the development of investigations on adjuvant properties of mycobacterial cells (preparations BCG, Freund's complete adjuvant) it has been found that numerous glycopeptides recovered from bacterial cell walls are strong adjuvants (cf. Ellous F., Adam A., Ciorbaru R., Lederer E., Bioch. Bioph. Res. Comm. 59, No. 4, 1317 (1974)).

(Adjuvants are compounds causing non-specific stimulation of the immune system of a human being and animals which results in an increased production of antibodies and in an enhancement of protective reaction of the organism, against e.g. infection, is increased. Adjuvants are used in medicine for the manufacture of vaccines and sera).

BACKGROUND OF THE INVENTION

Known in the art (Kusumoto S., Tarumi Y., Ikenaka K., Shiba T., Bull. Chem. Soc. (Japan) 49, (2), 533–539 (1976); and Lefrancier P., Choay J., Derrien M., Lederman I., Int. J. Pept. Protein Res., 9, No. 4, 249–257 (1977) is synthesis of certain fragments and analogues of glycopeptides of cell walls of bacteria, namely N-acetylmuramylpeptides of the formula:

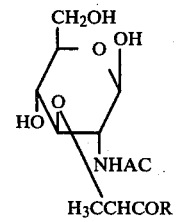

wherein R is residues of aminoacids or peptides such as Ala, Gly, Ala-D-Glu, Ala-D-Glu-NH₂,

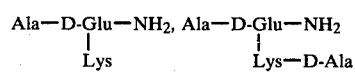

D-Ala-D-Glu-NH₂ and the like.

The synthesis comprises condensation of benzyl esters of corresponding aminoacids or peptides with blocked N-acetylmuramic acid.

This prior art method for the preparation of said glycopeptides has a disadvantage residing in that into the condensation reaction only blocked N-acetylmuramic acid (benzyl-2-acetamido-4,6-benzylidene-3-O-/D-1'-carboxyethyl/-2-deoxy-α-D-glucopyranoside/ is introduced which is preliminary synthetized in three stages from N-acetylglucosamine with a yield of 17–22% following the below-given scheme:

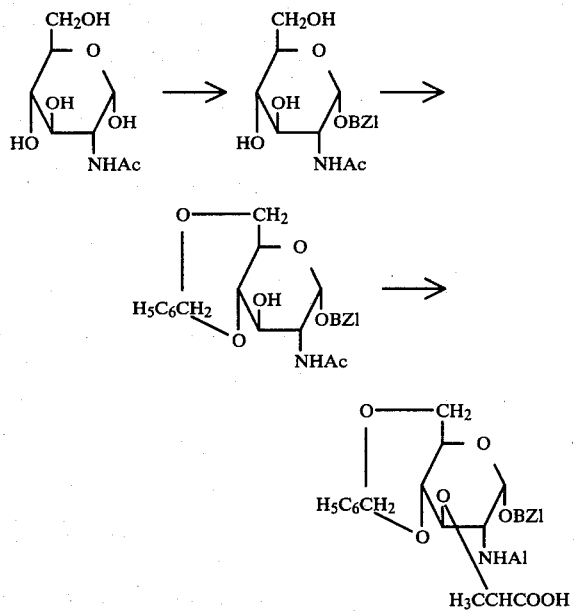

Some of the above-mentioned synthetic N-acetyl-muramylpeptides are strong adjuvants.

In a joint paper by Soviet and Bulgarian scientists Kotani S., Watanabe Y., Kinoshita F., Shimono T., Morisaki I., Shiba T., Kusumto S., Tarumi Y., Ikenaka K., Biken J. 18, 105 (1975)) it has been shown that a mixture of glycopeptides isolated from cell walls of *Lactobacillus bulgarieus* has an unusual antitumor activity: neutral glycopeptides of *Lactobacillus bulgarieus* cause necrosis of the tumor tissue on mice with sarcoma S-180 (Bogdanov I. G., Dalev P. G., Gurevich A. I., Kolosov M. N., Malkova V. P., Plemyannikova L. A., Sorokina I. B., Febs. Letters 57, No. 3, 259 (1975)). The synthesis of these glycopeptides is hitherto unknown.

The detection of biological activity (adjuvant activity and ability to cause necrosis in a tumor tissue) of glycopeptides isolated from cell walls of bacteria has given impetus to a synthetic preparation of various fragments of naturally-occurring glycopeptides and analogues thereof necessary for a profound investigation of biological activity of these compounds.

Analysis of fragments of glycopeptides isolated from cell walls of different microorganisms and demonstrating adjuvant activity, as well as analysis of glycopeptides of Lactobacillus bulgarieus revealing an unusual antitumor activity has shown that both N-acetylmuramic acid and N-acetyl-glucosamine are incorporated in the sugar part of the molecules of glycopeptides. However, the synthesis of glycopeptides containing, apart from N-acetylmuramic acid, N-acetylglucosamine, i.e. the synthesis of N-acetylglucosaminyl-N-acetylmuramylpeptides has not been hitherto known from the literature. The prior art method for the synthesis of said muramylpeptides makes it possible to obtain only N-acetylmuramylpeptides. The multi-stage synthesis scheme employed for this purpose is unsuitable in principle for association of the residue of N-acetylglucosamine with N-acetylmuramic acid by means of the bond 1→4 (all residues of aminosugars in any glycopeptide of cell walls of bacteria are interconnected by the bond 1→4). Therefore, the known method for preparing N-acetylmuramylpeptides cannot be used for the synthesis of N-acetylglucosaminyl-/1→4/-N-acetyl muramylpeptides. This defined the attempts in finding a new method for the preparation of various fragments and analogues of naturally-occurring glycopeptides of cell walls of bacteria.

OBJECT OF THE INVENTION

It is an object of the present invention to provide novel biologically active synthetic glycopeptides incorporating in the sugar part of their molecules various fragments of aminosugars of the type normally found in the cell walls of bacteria and to develop also a novel method for the preparation of said glycopeptides.

SUMMARY OF THE INVENTION

The object of the present invention is accomplished by glycopeptides of the formula (I) hereinbelow, wherein n=1 or 2, R is a residue of an aminoacid or linear peptides built of 2 to 5 amino acid residues.

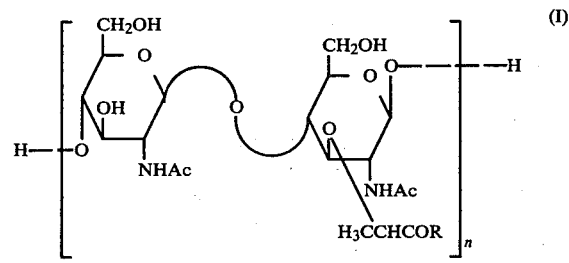

Glycopeptides of this formula are novel chemical compounds. It has been found that said compounds are biologically active and useful in medicine. The synthesis and biological activity of the glycopeptides according to the present invention have not been hitherto described in the literature.

The object of the present invention is accomplished also by a novel method of preparing glycopeptides of formula (I) which comprises condensation of unblocked (unprotected) muramyl-containing N-acetylaminosugars of the formula:

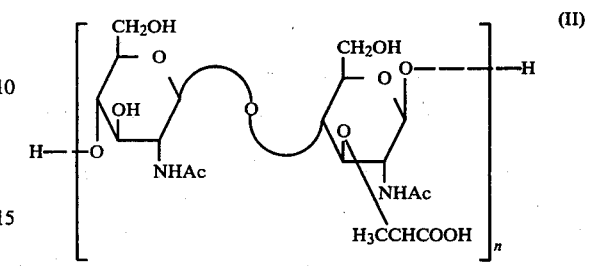

wherein n=1, 2 with blocked linear peptides by way of activation of the carboxy group of said aminosugars.

The method according to the present invention provides broad opportunities for the preparation of a number of naturally-occurring glycopeptides and analogues thereof by way of synthesis.

Other objects and advantages of the present invention will now become more fully apparent from the following detailed description.

DETAILED DESCRIPTION OF THE INVENTION

As it has been already mentioned hereinbefore, the method according to the present invention for the synthesis of glycopeptides of the general formula (I) comprises condensation of the sugar component with blocked linear peptides. Said method is characterized by unblocked muramyl-containing N-acetylaminosugars of formula (II) being introduced into the reaction of condensation as the sugar component.

The condensation reaction is conducted in an inert solvent medium, preferably in the presence of a condensation agent such as Woodward reagent (N-ethyl-5-phenyl-isoxazolium-3'-sulphonate) at a temperature within the range of from 0° to 25° C. in one stage.

The subsequent removal of the blocking groups from the aminoacid or peptide residue is effected by conventional techniques.

The starting aminosugars of formula (II) are isolated from the biomass of Micrococcus lysodeicticus, since the synthesis of such muramyl-containing N-acetylaminosugars is not known.

The employed method for isolating aminosugars of formula (II) from the biomass is known and described in the literature. It involves enzymatic hydrolysis of the biomass of Micrococcus lysodeikticus by means of lysozyme and a further two-stage purification in columns packed with Dowex 50×8 (H+-form) with particles of 200–400 mesh and Dowex 1×8 (CH₃COO⁻-form) 200–400 mesh (Hoshino O., Zenavi U., Sinay P., Jeanloz R. W., J. Biol. Chem. 247, No. 2, 381 (1972); and Sharon N., Osawa T., Flowers H. M., Jeanloz R. W., J. Biol. Chemistry, 241, 223 (1966)).

Analysis data for aminosugars of formula (II): GleNAc-/1→4/MurNAc: aminoacid and aminosugar analysis /6 N HCl, 2 and 24 hours, 100° C./Mur:GlcNH₂ 1.0:1.0 /2 hours/, 1.00:1.03 /24 hours with the account of decomposition/, no aminoacids;

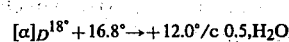

$[\alpha]_D^{16°} +15.2° \rightarrow +10.2°/c0.5, H_2O, 24\ hours/$,

Found, %: C,43.88; H,6.70; N,5.00. Calculated for $C_{19}H_{32}N_2O_{13}.1.5\ H_2O$: C,43.59; H,6.74; N,5.30.

GlcNAc/1→4/MurNAc/1→4/GlcNAc/1→4/MurNAc aminoacid and aminosugar analysis: /6 N HCl, 100° C., 16 and 24 hours/, Mur:GlcNH₂ 1.0:1.0 /with the account of decomposition at the 16-th hour/ and 1.00:1.04 (with the account of decomposition at 24 hours/, no aminoacids;

$[\alpha]_D^{18°} -10.4° \rightarrow -13.1°/c0.5, H_2O, 24\ hours/$

Found, %: C,44.50; H,5.63; N, 5.00. Calculated for $C_{38}H_{62}N_4O_{25}.3H_2O$, %: C,44.35; H,6.60; N, 5.45.

The starting blocked aminoacids or peptides employed for the synthesis are obtained by known methods of the peptide chemistry. In doing so, as a rule, use is made of benzyl ethers for blocking C-terminal carboxy groups and tert. butyloxycarbonyl and benzyloxycarbonyl groups for protection of free amino groups.

According to the present invention there are prepared glycopeptides of the general formula (I) including:

I. GlcNAc/1→4/MurNAc-Ala
N-acetylglucosaminyl/1→4/N-acetylmuramyl-alanine

II. GlcNAc/1→4/MurNAc-Ala-D-Glu-NH₂
N-acetylglucosaminyl/1→4/N-acetylmuramyl-alanyl-D-isoglutamine III. GlcNAc/1→4/MurNAc-Ala-D-Glu
N-acetylglucosaminyl/1→4/N-acetylmuramyl-alanyl-D-glutamic acid

IV.

GlcNAc/1 ⟶

4/MurNac—Ala—D-Glu—D-Asp—NH₂
                         |
                         Lys—D-Ala—NH₂ amide of N^ε-[N-acetylglucosaminyl/1→4/N-acetylmuramyl-alanyl-D-glutamyl-D-iso-asparaginyl]-lysyl-D-alanine

V.

GlcNAc/1 ⟶ 4/MurNAc/1 ⟶
                |
                Ala—D-Glu—NH₂

4/GlcNAc/1 ⟶ 4/MurNAc
                   |
                 Ala—D-Glu—NH₂

/1→4/-bis-[N-acetylglucosaminyl/1→4/N-acetylmuramyl-alanyl-D-isoglutamine]

The above-listed compounds comprise lyophilically dried white hygroscopic powders soluble in water, physiological solution, methanol or 50% ethanol, but insoluble in ether, benzene, petroleum ether or chloroform. These compounds possess a biological activity. As to the nature of this biological activity, these glycopeptides principally differ from antitumor preparations employed currently in oncological practice. The currently employed preparations, as a rule, cause merely retardation of the tumor growth and this effect is most pronounced at the early stages of the malignant tumor growth, i.e. the known currently employed preparations are effective in the treatment of early stages of the disease. All of them are substantially cytotoxic in respect of cells of normal tissues as well, they frequently show immunodepressant properties, inhibit hemopoiesis (hematoplasty). In contrast thereto, the biological activity of the synthetic glycopeptides according to the present invention is revealed in a rapid selective necrosis of a strongly developed tumor and a subsequent retardation of the tumor growth even after a single injection of the compound. Normal tissues are not injured therewith. All the glycopeptides according to the present invention are of low toxicity and cause no inhibition of hemopoiesis.

Biological tests have been performed on mice with a 8-day Krocker sarcoma (S-180): intravenous administration (dose of 50 to 100 mg/kg/; necrosis evaluation after 24 hours (4–6 as of the 6-point scale), measurement of volume (or weight) of the tumor after 4–5 days (growth inhibition of up to 70%). For example, upon a single intravenous administration of N-acetylglucosaminyl/1→4/N-acetylmuramyl-alanyl-D-isoglutamine (Compound II) to mice with a 8-day sarcoma S-180 (strongly developed tumor) in the dose of 100 mg/kg with four out of five test animals a selective necrosis of the tumor tissue covering substantially the entire tumor is observed 24 hours after administration, while after 5 days 70% inhibition of the growth of the malignant tumor occurs as compared to the control animals. Therewith, no signs of toxicity are noticed, hemopoiesis is not inhibited, the number of leukocytes is substantially increased.

We have demonstrated that the necrosis is not caused by the constituent components of said glycopeptides: N-acetylglucosamine (VI), N-acetylmuramic acid (VII), N-acetylglucosaminyl/1→4/N-acetylmuramic acid (VIII), N-acetylglucosaminyl /1→4/-N-acetylmuramyl/1→4/N-acetylglucosaminyl/1→4/N-acetylmuramic acid (IX) or by peptides employed for the synthesis of compounds I to V: Ala-D-Glu-NH₂ (X), Ala-D-Glu (XI), Ala—D-Glu—D-Asp—NH₂
            |
            Lys—D-Ala—NH₂

All these data are shown in the Table following the Examples.

For a better understanding of the present invention some specific Examples illustrating preparation of glycopeptides are given hereinbelow.

Melting temperatures are determined in the Koffler block (temperatures are corrected). Aminoacid and aminosugar analyses are carried out using an automatic aminoacid analyser Liquimat (produced by Labotron company). Rotation angles are determined on Perkin-Elmer polarimeter 141. The systems for thin-layer chromatography (TLC): n-BuOH:EtOH:H₂O 3:6:1 (A);

n-BuOH:AcOH:H$_2$O 3:1:1 (B), n-BuOH:AcOH:H$_2$O 2:1:1 (C).

EXAMPLE 1

N-acetyl-glucosaminyl/1→4/N-acetylmuramylalanine (I)

(a) To a solution of 160 mg (0.33 mM) of N-acetyl-glucosaminyl/1→4/N-acetylmuramic acid in 8 ml of dimethylformamide (DMFA) at the temperature of 0° C. there are added 0.05 ml of triethylamine (TEA) and 150 mg (0.45 mM) of Woodward reagent K; the mixture is stirred for 1 hour at 0° C. and then for one more hour at the temperature of 20° C. till complete dissolution. A solution of 90 mg (0.3 mM) of nitrobenzyl ether of alanine bromohydrate and 0.05 ml of triethylamine (TEA) in 4 ml of DMFA are dropwise added under stirring for 15 minutes and stirring is continued for 20 hours at room temperature. The residue after evaporation in vacuum is dissolved in 1 ml of a 50% aqueous ethanol and passed through a column /10 ml/ with packing of Dowex 50×8 (H$^+$-form) and then through a column /10 ml/ packed with Dowex 1×8 (CH$_3$COO$^-$-form), in both cases elution being effected by means of a 50% aqueous ethanol. The residue after evaporation of the eluate is resettled from methanol by means of ether. There are produced 80 mg (33.0%) of nitrobenzyl ether of N-acetylglucosaminyl/1→4/N-acetylmuramylalanine. 50 mg of the latter are dissolved in a 75% aqueous acetic acid and hydrogenated over Pd-black for 6 hours. The catalyst is filtered-off and the residue after evaporation is resettled from methanol by ether to give 30 mg /80%/ of the product (I). Found, %: C,44.41; H,6.78; N,7.06; Calculated for C$_{22}$H$_{37}$N$_3$O$_4$.1.5H$_2$O,%: C, 44.44; H,6.78; N,7.07. Aminoacid and aminosugar analyses: /A.A.A./ (6 N HCl, 100° C., 16 hours): Ala:-Mur:GlcNH$_2$ 1:1.08:1.1 (with the account of decomposition at the 16-th hour of hydrolysis); $[\alpha]_D^{18°} -3.5°$(c 0.5, H$_2$O) M.p. 150° C. (with decomposition). Thin-layer chromatography (TLC): R$_f$=0.45.

System A (b) To a solution of 0.16 g (0.33 mM) of N-acetyl-glucosaminyl/1→4/N-acetylmuramic acid and 0.045 ml of TEA in 10 ml of DMFA under stirring at −15° C. there is added 0.045 ml (0.33 mM) of isobutylchloroformiate. Two minutes after a solution of 0.07 g (0.22 mM) of bromohydrate of nitrobenzyl ether of alanine cooled to −15° C. and 0.036 ml of TEA in 10 ml of DMFA are added thereto. The solution is maintained for three hours at the temperature of −15° C. under stirring. The residue after evaporation in vacuum is subjected to a further purification following the procedure of the foregoing Example 1(a) to give 24 mg (32%) of nitrobenzyl ether of N-acetylglucosaminyl/1→4/N-acetyl-muramylalanine. After the removal of the blocking group as described in Example 1(a) hereinabove, there are obtained 17 mg /80%/ of the product (I).

EXAMPLE 2

N-acetylglucosaminyl/1→4/N-acetylmuramyl-alanyl-D-isoglutamine (II)

The reaction of condensation is conducted as described in the foregoing Example 1(a) starting from 130 mg (0.3 mM) of benzyl ether of alanyl-D-isoglutamine trifluoroacetate. The reaction mixture is evaporated to a small (about 1 ml) volume; the precipitate settled-out by means of n-butanol is filtered-off and dissolved in 1 ml of a 50% aqueous ethanol; further purification is conducted following the procedure of Example 1 to give 75 mg (31%) of benzyl ether of N-acetyl glucosaminyl/1→4/N-acetylmuramyl-alanyl-D-isoglutamine.

Hydrogenation over Pd-black is effected as in Example 1 with 50 mg of said benzyl ether. There are obtained 36 mg (81%) of the product (II). Found, %: C,39.64; H,7.11; N,8.41; calculated for C$_{27}$H$_{45}$N$_5$O$_{16}$.7-H$_2$O, %: C,39.22; H,7.23; N,8.51. M.W. 695, 697; A.A.A.: (6 N HCl, 100°, 16 hours): Ala-Glu:-Mur:GlcNH$_2$ 1:0.81:1.01:1.02 (6 N HCl, 100°, 24 hours) 1:0.96:0.96:1.2 (with the account of decomposition at 16 and 24 hours respectively); $[\alpha]_D^{20°} +2.8°$ (c with 0.5, H$_2$O, after 5 minutes), 0° C. (c 0.5, H$_2$O, after 22 hours), M.p. 170° C. with decomposition; TLC: R$_f$=0.3 (System A), R$_f$=0.45 (System C).

EXAMPLE 3

N-acetylglucosaminyl/1→4/N-acetylmuramyl-alanyl-D-glutamic acid (III)

The reaction of condensation and treatment of the reaction mixture are conducted following the procedure described in the foregoing Example 1a, with 310 mg (0.6 mM) of dibenzyl ether of alanyl-D-glutamic acid trifluoroacetate. There are obtained 200 mg (38%) of dibenzyl ether of N-acetylglucosaminyl/1→4/N-acetylmuramyl-alanyl-D-glutamic acid; after the removal of benzyl blocking groups by hydrogenolysis over Pd-black from 100 mg of said dibenzyl ether there are obtained 64 mg (80%) of the product (III). Found, %: C,43.00; H,6.71; N,7.30. Calculated for C$_{27}$H$_{44}$N$_4$O$_{17}$.3H$_2$O, %: C,43.19; H,6.71; N,7.46. M.W. (molecular weight): 696, 681. A.A.A. (6 N HCl, 100° C., 24 hours): Ala÷Glu:Mur:GlcNH$_2$ 1.04:1.00:0.96:1.00 (with the account of decomposition at the 24-th hour). $[\alpha]_D^{18°} -4.2°$ (with 0.5 H$_2$O), M.p. 170° C. (decomposition), TLC: R$_f$=0.2 (System A).

EXAMPLE 4

Amide of N$^\epsilon$-[N-acetylglucosaminyl/1→4/N-acetylmuramyl-alanyl-D-glutamyl-D-iso-asparaginyl]-lysyl-D-alanine (IV)

The condensation reaction is conducted as described in Example 1(a) hereinbefore with 300 mg (0.34 mM) of amide of N$^\alpha$-carbobenzoxy N$^\epsilon$[alanyl-(γ-benzyl)-D-glutamyl-D-isoasparaginyl]-lysyl-D-alanine trifluoroacetate. The reaction mixture is evaporated to the volume of about 1 ml, the condensation product is precipitated with water, washed with water, methanol and ether to give 136 mg (27%) of amide of N$^\alpha$-carbobenzoxy-N$^\epsilon$-[N-acetylglucosaminyl/1→4/N-acetomuramyl-alanyl-(α-benzyl)-D-glutamyl-D-iso-asparaginyl]-lysyl-D-alanine and, after the removal of benzyloxycarbonyl and benzyl protective groups by hydrogenolysis over Pd-black, from 50 mg there are produced 35 mg (83%) of the product (IV). Found, %: C,52.32; H,6.55; N,11.00; calculated for C$_{55}$H$_{80}$N$_{10}$O$_{22}$.1.5H$_2$O, %: C,52.41; H,6.63; N,11.11. M.W. 1,233.32; A.A.A. (6 N HCl, 100° C., 16 hours): Asp:Lys:Glu:Ala:-Mur:GlcNH$_2$ 1.00:0.96:1.04:2.20:1.00:0.80 (with the account of decomposition at the 16-th hour). TLC: R$_f$=0.3 (System B).

EXAMPLE 5

1→4/bis-[N-acetylglucosaminyl/1→4/N-acetylmuramyl-alanyl-D-isoglutamine] (V)

The reaction of condensation is conducted following the procedure described in Example 1(a) hereinbefore with 243 mg (0.25 mM) of N-acetylglucosaminyl/1→4/-Nacetylmuramyl/1→4N-acetylglucosaminyl/1→4/N-acetylmuramic acid and 210 mg (0.5 mM) of benzyl either of alanyl-D-isoglutamine trifluoroacetate. The reaction mixture is evaporated to the volume of about one ml, added with 80% of water, filtered and passed successively through columns filled with Dowex 50×8 (H+-form) and Dowex 1×8 (CH$_3$COO−-form). The resulting 50 mg of crude condensation product are divided in preparative plates "Merck" in the system n-BuOH:EtOH:H$_2$O 3:6:1 to give 18 mg of /1→4/-bis[N-acetylglucosaminyl/1→4/N-acetylmuramylalanyl-(α-benzyl)-D-isoglutamine] and, after the removal of benzyl protective groups there are obtained 10 mg of the product (V). Found, %: C,44.01; H,6.74; N,9.44; Calculated for C$_{53}$H$_{86}$N$_{10}$O$_{29}$.6H$_2$O %: C,44.34; H,6.88; N, 9.76; M.W. 1,327; 351; A.A.A. (6 N HCl, 100° C., 16 hours), Ala÷Glu:Mur:GlcNH$_2$ 1.00:1.01:1.00:1.05; TLC: R$_f$=0.1 (System C).

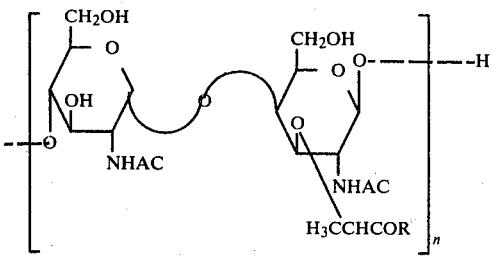

where n=1 or 2; R is a residue of a linear peptide of 2 to 5 amino acids and Ac is acetyl.

2. A glycopeptide as claimed in claim 1, wherein n=1, R=Ala-D-Glu-NH$_2$.

3. A glycopeptide as claimed in claim 1, wherein n=1, R=Ala-D-Glu.

4. A glycopeptide as claimed in claim 1, wherein n=1, R=

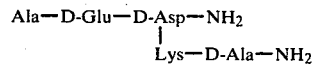

5. A glycopeptide as claimed in claim 1, wherein n=2, R=Ala-D-Glu-NH$_2$.

6. A glycopeptide of the general formula:

TABLE

| | Compound | Dose, mg/kg | Necrotic reaction shown after 24 h, number of animals | Inhibition of the tumor growth, % of the control | Death of animals |
|---|---|---|---|---|---|
| I. | N—acetylglucosaminyl/1→4/N—acetylmuramyl-alanine | 100 | 3/5 | 19 | 0 |
| | | 50 | 2/5 | 17 | 0 |
| II. | N—acetylglucosaminyl/1→4/N—acetylmuramylalanyl-D-iso-glutamine | 100 | 4/5 | 70 | 0 |
| | | 50 | 8/10 | 12 | 0 |
| III. | N—acetylglucosaminyl/1→4/N—acetylmuramulalanyl-D-glutamic acid | 100 | 3/5 | 45 | 0 |
| | | 50 | 4/10 | +28 | 0 |
| IV. | Amide of N$^ε$[N—acetylglucosaminyl/1→4/N—acetylmuramylalanyl-D-glutamyl-D-iso-asparaginyl]-lysyl-D-alanine | 100 | 3/5 | 41 | 0 |
| | | 50 | 3/5 | 23 | 0 |
| V. | /1→4/-bis-[N—acetylglucosaminyl/1→4/N—acetylmuramylalanyl-D-isoglutamine] | 50 | 3/5 | 66 | 0 |
| | Constituents of said compounds | | | | |
| VI. | N—acetylglucosamine | 250 | 0.5 | 0 | 0 |
| VII. | N—acetylmuramic acid | 250 | 0/8 | 52 | 25 |
| | | 100 | 0/8 | 37 | 0 |
| VIII. | N—acetylglucosaminyl/→4/ N—acetylmuramic acid | 250 | 0/10 | 0 | 0 |
| | | 100 | 0/10 | 0 | 0 |
| IX. | N—acetylglucosaminyl/1→4/N—acetylmuramyl/1→4/N—acetylglucosaminyl-/1→4/N—acetylmuramic acid | 250 | 0/10 | 0 | 0 |
| X. | Alanyl-D-iso-glutamine | 100 | 0/10 | +28 | 0 |
| XI. | Alanyl-D-glutamic acid | 100 | 0/8 | 37.3 | 0 |
| XII. | Amide of N$^ε$[Alanyl-D-glutamyl-D-iso-asparaginyl]-lysyl-D-alanine | 250 | 0/5 | 0 | 0 |

What is claimed is:

1. Glycopeptides of the general formula:

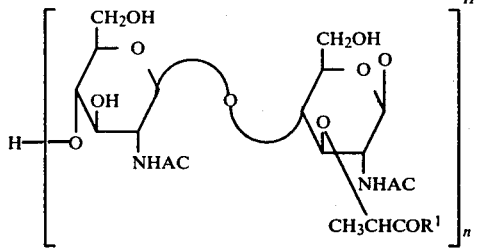

wherein n is 1 or 2 and $R^1$ is selected from the group consisting of Ala-D-Glu,

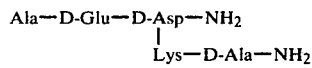

and Ala-D-Glu-$NH_2$ and Ac is acetyl.

7. Compounds of the Formula:

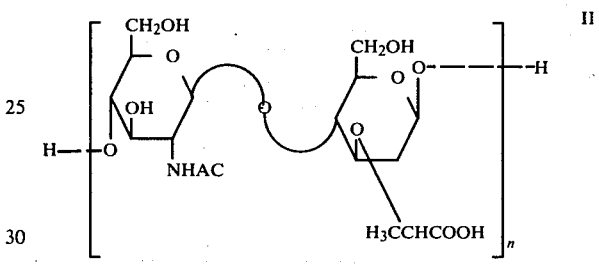

wherein Ac is acetyl; R is a dipeptide.

8. A method of inhibiting the growth of tumors in mammals which comprises administering thereto an effective amount of a compound as claimed in claim 1.

9. A method for preparing glycopeptides as claimed in claim 1, 2, 3, 4, 5, 6 or 7 comprising condensation of non-blocked muramyl-containing N-acetyl aminosugars of the formula:

wherein n = 1 or 2 and Ac is acetyl with protected linear peptides as defined in, said reaction proceeding by activation of the moiety of said unprotected aminosugars of formula II and participation of these activated aminosugars in the coupling reaction.

* * * * *